US00PP25837P2

(12) United States Plant Patent
Rutten

(10) Patent No.: US PP25,837 P2
(45) Date of Patent: Aug. 25, 2015

(54) ***HYDRANGEA* PLANT NAMED 'WRHPBB2'**

(50) Latin Name: *Hydrangea paniculata*
Varietal Denomination: WRHPBB2

(71) Applicant: Catherien Rutten, Leende (NL)

(72) Inventor: Catherien Rutten, Leende (NL)

(73) Assignee: Spring Meadow Nursery Inc., Grand Haven, MI (US)

( * ) Notice: Subject to any disclaimer, the term of this patent is extended or adjusted under 35 U.S.C. 154(b) by 133 days.

(21) Appl. No.: 13/987,986

(22) Filed: Sep. 20, 2013

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — Anne Grunberg
(74) *Attorney, Agent, or Firm* — C. A. Whealy

(57) ABSTRACT

A new and distinct cultivar of *Hydrangea* plant named 'WRHPBB2', characterized by its upright, outwardly spreading and mounded plant habit; strong and sturdy stems; dark green-colored leaves; large mophead-type inflorescences with sterile flowers with relatively large white-colored sepals; and good winter hardiness.

2 Drawing Sheets

Botanical designation: *Hydrangea paniculata.*
Cultivar denomination: 'WRHPBB2'.

BACKGROUND OF THE INVENTION

The present invention relates to a new and distinct *Hydrangea* plant, botanically known as *Hydrangea paniculata* and hereinafter referred to by the name 'WRHPBB2'.

The new *Hydrangea* plant is a product of a planned breeding program conducted by the Inventor in Leende, The Netherlands. The objective of the breeding program was to develop new *Hydrangea* plants with strong stems and large attractive inflorescences.

The new *Hydrangea* plant originated from an open-pollination during the spring of 2005 of *Hydrangea paniculata* 'Barbara', disclosed in U.S. Plant Pat. No. 13,606, as the female, or seed parent with an unknown selection of *Hydrangea paniculata* as the male, or pollen, parent. The new *Hydrangea* plant was discovered and selected by the Inventor as a single flowering plant from within the progeny of the stated open-pollination in a controlled environment in Leende, The Netherlands in the spring of 2008.

Asexual reproduction of the new *Hydrangea* plant by softwood cuttings in a controlled environment in Leende, The Netherlands since the spring of 2008 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'WRHPBB2'. These characteristics in combination distinguish 'WRHPBB2' as a new and distinct *Hydrangea* plant:

1. Upright, outwardly spreading and mounded plant habit.
2. Strong and sturdy stems.
3. Dark green-colored leaves.
4. Large mophead-type inflorescences with sterile flowers with relatively large white-colored sepals.
5. Good winter hardiness.

Plants of the new *Hydrangea* differ from plants of the female parent, 'Barbara', in the following characteristics:

1. Plants of the new *Hydrangea* have stronger stems than plants of 'Barbara'.
2. Plants of the new *Hydrangea* have stronger and healthier leaves than plants of 'Barbara'.

Plants of the new *Hydrangea* can be compared to plants of *Hydrangea paniculata* 'Pinky Winky', not patented. In side-by-side comparisons, plants of the new *Hydrangea* differed primarily from plants of 'Pinky Winky' in the following characteristics:

1. Plants of the new *Hydrangea* had larger inflorescences than plants of 'Pinky Winky'.
2. In the autumn, sterile flowers of plants of the new *Hydrangea* retained their white coloration whereas sterile flowers of plants of 'Pinky Winky' became dark pink in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'WRHPBB2' grown in an outdoor nursery.

The photograph on the second sheet is a close-up view of a typical inflorescence of 'WRHPBB2'.

DETAILED BOTANICAL DESCRIPTION

Plants used for the aforementioned photographs and the following description were grown during the summer in ground beds in an outdoor shadehouse in Grand Haven, Mich. and under cultural practices typical of commercial *Hydrangea* production. Plants of the new *Hydrangea* were four years old when the photographs and description were taken. In the following description, color references are made to The Royal Horticultural Society Colour Chart, 1995 Edition, except where general terms of ordinary dictionary significance are used.

Botanical description: *Hydrangea paniculata* 'WRHPBB2'.

Parentage:

*Female, or seed, parent.*—*Hydrangea paniculata* 'Barbara', disclosed in U.S. Plant Pat. No. 13,606.

*Male, or pollen, parent*.—Unknown selection of *Hydrangea paniculata*, not patented.

Propagation:

*Type cutting*.—By softwood cuttings.

*Time to initiate roots, summer*.—About 18 days at temperatures about 24° C.

*Time to produce a rooted young plant, summer*.—About three months at temperatures about 24° C.

*Root description*.—Fine and thick; white and brown in color.

*Rooting habit*.—Freely branching; dense.

Plant description:

*Plant form and growth habit*.—Perennial deciduous shrub; upright, outwardly spreading and mounded plant habit; inverted triangle; strong and sturdy lateral branches; freely branching habit with about 24 lateral branches developing per plant; vigorous growth habit.

*Plant height*.—About 105 cm.

*Plant diameter or area of spread*.—About 145 cm.

*Lateral branches*.—Length: About 82 cm. Diameter: About 5 mm. Internode length: About 6 cm. Texture: Smooth, glabrous. Strength: Strong, sturdy. Color: Close to 187A.

Leaf description:

*Arrangement*.—Opposite, simple.

*Length*.—About 12 cm.

*Width*.—About 6.5 cm.

*Shape*.—Elliptic.

*Apex*.—Ovate.

*Base*.—Obtuse.

*Margin*.—Serrulate.

*Texture, upper and lower surfaces*.—Coarse, pubescent.

*Venation pattern*.—Pinnate.

*Color*.—Developing and fully expanded leaves, upper surface: Close to 138A; venation, close to 145B. Developing and fully expanded leaves, lower surface: Close to 138B; venation, close to 145C.

*Petioles*.—Length: About 2 cm. Diameter: About 1 mm. Texture, upper and lower surfaces: Pubescent. Color, upper surface: Close to 59A. Color, lower surface: Close to 145A.

Flower description:

*Flower type and habit*.—Single sterile and fertile flowers arranged on terminal mophead cymes; flowers face mostly outwardly.

*Fragrance*.—Moderately fragrant; pleasant.

*Natural flowering season*.—Plants flower throughout the summer in Grand Haven, Mich.; flowers not persistent.

*Quantity of flowers*.—Freely flowering habit; about 32 fertile flowers and about 19 sterile flowers develop per inflorescence.

*Inflorescence height*.—About 8.5 cm.

*Inflorescence diameter*.—About 10.5 cm.

*Flower diameter, fertile flowers*.—About 6 mm.

*Flower depth (height), fertile flowers*.—About 3 mm.

*Flower diameter, sterile flowers*.—About 4.5 cm.

*Flower depth (height), sterile flowers*.—About 3 mm.

*Flower buds, fertile and sterile flowers*.—Length: About 5 mm. Diameter: About 4 mm. Shape: Obovate. Color: Close to 155B.

*Petals, fertile flowers only*.—Quantity per flower and arrangement: About five in a single whorl. Length: About 3 mm. Width: About 2 mm. Shape: Ovate. Apex: Acute. Base: Cuneate. Margin: Entire. Texture, upper and lower surfaces: Smooth, glabrous. Color: When opening, upper and lower surfaces: Close to 155D. Fully opened, upper and lower surfaces: Close to 155D.

*Sepals, fertile flowers*.—Quantity per flower and arrangement: About four to six in a single whorl. Length: About 1 mm. Width: About 0.5 mm. Shape: Subulate. Apex: Acute. Base: Obtuse. Margin: Entire. Texture, upper and lower surfaces: Smooth, glabrous. Color: When opening, upper and lower surfaces: Close to 142D. Fully opened, upper and lower surfaces: Close to 142D.

*Sepals, sterile flowers*.—Quantity per flower and arrangement: About four to six in a single whorl. Length: About 2 cm. Width: About 3 cm. Shape: Ovate. Apex: Broadly acute. Base: Obtuse. Margin: Entire. Texture, upper and lower surfaces: Smooth, glabrous. Color: When opening, upper and lower surfaces: Close to 155C. Fully opened, upper and lower surfaces: Close to 155C.

*Pedicels, fertile flowers*.—Angle: About 20° to 30° from inflorescence axis. Strength: Strong, sturdy. Length: About 6 mm. Diameter: About 1 mm. Texture: Pubescent. Color: Close to 145C.

*Pedicels, sterile flowers*.—Angle: About 30° to 40° from inflorescence axis. Strength: Strong, sturdy. Length: About 2 cm. Diameter: About 1 mm. Texture: Pubescent. Color: Close to 8D.

*Reproductive organs, fertile flowers*.—Stamens: Quantity per flower: About eight. Anther shape: Round. Anther length: About 1 mm. Anther color: Close to 197A. Pollen amount: Scarce. Pollen color: Close to 4D. Pistils: Pistil quantity per flower: About two. Pistil length: About 3 mm. Stigma shape: Round. Stigma color: Close to 150D. Style length: About 1 mm. Style color: Close to 150D. Ovary color: Close to 145C.

*Reproductive organs, sterile flowers*.—Stamens: None observed on plants of the new *Hydrangea*. Pistils: None observed on plants of the new *Hydrangea*.

*Seeds, fertile flowers only*.—Quantity per inflorescence: Numerous. Size: Less than 0.1 mm by less than 0.1 mm; dust-like. Color: Brown.

Disease & pest resistance: Plants of the new *Hydrangea* have been observed to have resistance to root rot pathogens common to *Hydrangea* plants. Plants of the new *Hydrangea* have not been observed to be resistant to pests and other pathogens common to *Hydrangea* plants.

Temperature tolerance: Plants of the new *Hydrangea* have been shown to be tolerant to temperatures ranging from about −31° C. to about 38° C.

It is claimed:

1. A new and distinct *Hydrangea* plant named 'WRHPBB2' as illustrated and described.

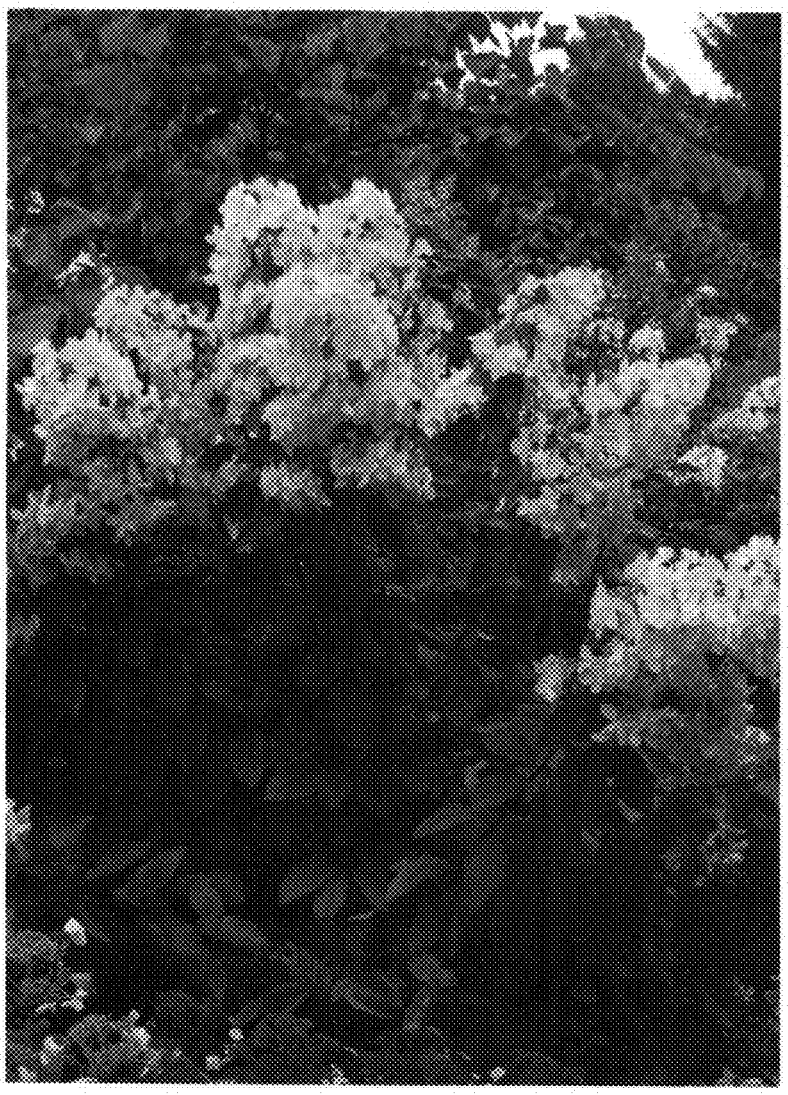

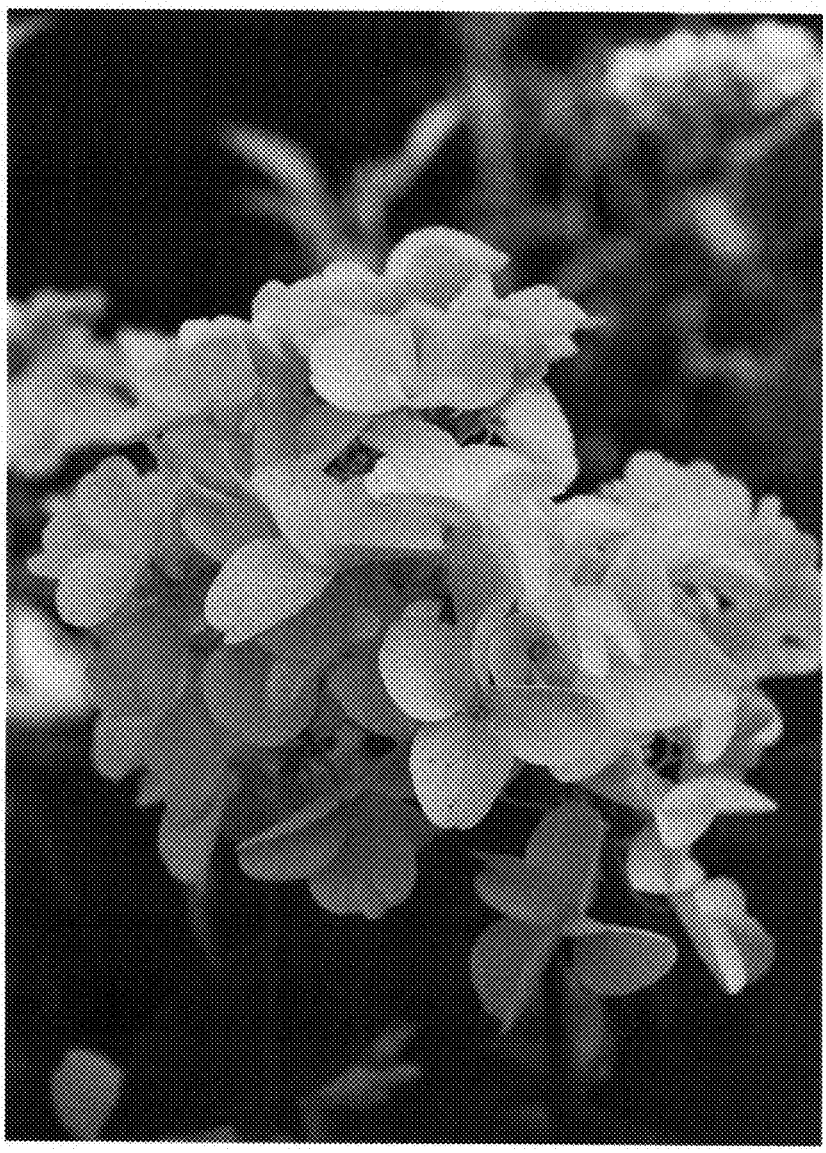

* * * * *